United States Patent [19]

Nelson

[11] Patent Number: 4,668,828

[45] Date of Patent: May 26, 1987

[54] CONVERSION OF PROSTAGLANDIN ANALOGS INTO A BICARBONATE SOLUBLE OLIGOMERIC MIXTURE

[75] Inventor: George L. Nelson, Narberth, Pa.

[73] Assignee: The United States of America as represented by the Secretary of the Navy, Washington, D.C.

[21] Appl. No.: 492,087

[22] Filed: May 6, 1983

[51] Int. Cl.$^4$ .............................................. C07C 45/70
[52] U.S. Cl. ..................................... 568/353; 568/379
[58] Field of Search ................................ 568/353, 379

[56] References Cited

U.S. PATENT DOCUMENTS 4,245,111  1/1981  Polis et al. ........................... 560/121
4,338,466  7/1982  Nelson ................................. 568/379

*Primary Examiner*—James H. Reamer
*Attorney, Agent, or Firm*—Prithvi C. Lall; Arthur A. McGill; Michael J. McGowan

[57] ABSTRACT

A method for oligomerization of a group of prostaglandin analogs such as the Ethyl Analog 3-(trans-3-keto-1-pentenyl)-2-ethyl-2-cyclopentenone into a biologically active exhibiting protection of oxidative phosphorylation of degenerated mitochondria and sodium bicarbonate soluble oligomeric mixtures is described. The Ethyl Analog is treated with ethanolic potassium hydroxide solution with exposure to atmospheric oxygen at moderate conditions of temperature, time and concentration.

5 Claims, No Drawings

CONVERSION OF PROSTAGLANDIN ANALOGS INTO A BICARBONATE SOLUBLE OLIGOMERIC MIXTURE

STATEMENT OF GOVERNMENT INTEREST

The invention described herein may be manufactured and used by or for the Government of the United States of America for governmental purposes without the payment of royalties thereon or therefor.

Subject patent application is related to my co-pending application Ser. No. 492,088, filed May 6, 1983 and entitled CONVERSION OF PROSTAGLANDIN ANALOGS INTO A BICARBONATE INSOLUBLE OLIGOMERIC MIXTURE.

BACKGROUND OF THE INVENTION (1) Field of the Invention

This invention is related to prostaglandin analogs and method of preparation thereof, as precursors for the synthesis of oligomeric mixtures showing biological activity with regard to restoration of oxidative phosphorylation in the degenerated mitocondria and more particularly to oligomerization of the Ethyl Analog having low molecular weights which give rise to oligomeric mixture having various components thereof biologically active in vitro.

(2) Description of the Prior Art

A new class of polymeric derivatives designated $PGB_x$ and the syntheses thereof are disclosed in U.S. Pat. No. 4,153,802 issued May 8, 1979 to David Polis et al, which have the unique property of restoring the in vitro oxidative phosphorylation ability of isolated degraded mitochondria. Furthermore, synthesis of prostaglandin analogs including the Ethyl Analog as defined below and related compounds is disclosed in U.S. Pat. No. 4,338,466 issued July 6, 1982 to George L. Nelson. All the aboveidentified patents are incorporated herein by reference. The analogs used in the syntheses are prostaglandins such as $PGB_1$, 13-14-dehydro-$PGB_1$ and 15-keto-$PGB_1$ methyl ester, each having a relatively complex molecular structure resulting in oligomeric derivatives which are not amenable to structural elucidation by conventional spectroscopic techniques necessary for defining the structureactivity relationships. Attempts by a number of research groups to resolve this complex mixture of oligomeric derivatives into individual components retaining biological activity have been unsuccessful.

Conversion of prostaglandin analogs such as 3-(trans-3-keto-1-pentenyl)-2-ethyl-2-cyclopentenone; hereinafter referred to as Ethyl Analog or E.A into a higher molecular weight distribution bicarbonate soluble oligomeric mixture by treatment with ethanolic potassium hydroxide (KOH solution diluted with ethanol) with exposure to atmospheric oxygen has been tried by our group. These prostaglandin analogs are represented by:

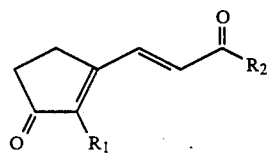

where $R_1$, and $R_2$ are members of the alkyl group. When $R_1$ and $R_2$ are $CH_2.CH_3$ each, the analog is called the Ethyl Analog (E.A.). However, the Ethyl Analog was oligomerized by treatment with ethanolic potassium hydroxide over a seven day period to give complex crude oligomeric mixture that was ca.60 percent soluble. Both the bicarbonate soluble and insoluble fractions obtained from the crude oligomeric mixture were fractionated on Sephadex LH-20, a substrate for size exclusion chromatography. Mitochondrial activity in the protection of oxidative phosphorylation was observed for both the bicarbonate soluble and insoluble fractions with generally higher activity being observed in the bicarbonate soluble fractions. Most notably, inhibition of mitochondrial activity at higher concentrations, as is observed in the case of $PGB_x$ derived from 15-keto-PGB1, was not observed for the oligomeric mixture derived from the Ethyl Analog. The activities observed for the oligomeric mixture derived from the E.A. were generally lower than those observed for 15-keto-PGB1 derived $PGB_x$ at concentrations where $PG_{Bx}$ exhibited maximum mitochondrial activity. However, at higher concentrations a greater protection was afforded by oligomeric fractions derived from the Ethyl Analog than that in the case of $PGB_x$. The mitochondrial activity for both the bicarbonate soluble and insoluble fractions derived from Sephadex LH-20 (substrate for size exclusion chromatography) chromatography was distributed throughout the fractions.

Although the above-indicated results held much potential, several serious problems remained in this method for conversion of the Ethyl Analog (E.A.) into a bicarbonate soluble oligomer possessing the ability to protect isolated mitochondria against the loss of oxidative phosphrylation. The problems were generally associated with the severe conditions (7-day treatment with ethanolic KOH) used for the conversion to a bicarbonate soluble oligomeric mixture that was a very complex mixture and not readily amenable to structural elucidation by spectroscopic methods. For this reason, a series of experiments needed to be carried out to find out how the bicarbonate soluble oligomer fraction can be maximized while reducing the severity of the reaction conditions, what is the functionality which gives rise to bicarbonate solubility and what molecular changes are involved in oligomer formation. It was on the basis of this investigation that conditions for the conversion of the Ethyl Analog to a bicarbonate soluble (acidic) oligomeric mixture, as described in subject patent application and for the formation of a bicarbonate insoluble (neutral) oligomeric mixture, as described in my copending patent application, were developed.

In summary, several aspects critical to the oligomerization of Ethyl Analog (E.A.) resulted from these investigations. It has been determined that sufficient exposure to oxygen is required for formation of the functionality responsible for bicarbonate solubility. This functionality has been identified as the carboxylic acid although the detailed mechanistic mode of formation of this acidic functional group from the neutral Ethyl Analog is not completely defined. Taking advantage of this information, the Ethyl Analog could be oligomerized to high conversions of bicarbonate soluble oligomer (greater than 80 percent) under relatively mild conditions (3–6 hours at 50° C.) if sufficient exposure to atmospheric oxygen was provided.

SUMMARY OF THE INVENTION

The method of conversion of the Ethyl Analog into a high molecular weight distribution bicarbonate soluble oligomeric mixture by treatment with ethanolic potassium hydroxide with exposure to atmospheric oxygen, according to the teachings of subject invention includes treatment of the Ethyl Analog (E.A.) with ethanolic potassium hydroxide solution under mild condition of 50° C. in a constant temperature bath with sufficient exposure to oxygen. The reaction is quenched by the addition of dilute hydrochloric acid to lower the pH of the solution mixture is extracted several times with ethyl acetate. The combined sodium bicarbonate extracts are then studied for oxidative phosphorylation of degenerated mitochondria in vitro.

An object of subject invention is to have a new technique for converting the Ethyl Analog (E.A.) into a higher molecular weight distribution sodium bicarbonate soluble oligomeric mixture which is active in oxidative phosphorylation of degenerated mitochondria.

Another object of subject invention is to have a method for converting the Ethyl Analog (E.A.) into high molecular weight sodium bicarbonate soluble oligomeric mixture by treatment with ethanolic potassium hydroxide with exposure to atmospheric oxygen.

Still another object of subject invention is to have a new technique for converting the Ethyl Analog in a higher molecular weight distribution which is formed under mild temperature conditions.

Still another object of subject invention is to oligomerize the Ethyl Analog (E.A.) into a biologically active oligomeric mixture where the time for the reaction to reach completion is relatively short.

Other objects, advantages and novel features of the invention will become apparent from the following detailed description of the invention.

DESCRIPTION OF A PREFERRED EMBODIMENT

A process for polymerizing the Ethyl Analog (E.A.) according to the teachings of subject invention includes treatment of the Ethyl Analog (E.A.) with an ethanolic solution of potassium hydroxide under mild conditions and for relatively short period. The reaction is then stopped by making the solution acidic, thus reducing the pH value thereof. The reaction is conducted in an atmosphere providing sufficient exposure to oxygen. The quenched reaction mixture is diluted with water and extracted several times with ethyl acetate followed by further extraction with sodium bicarbonate solution. The combined bicarbonate extracts are further acidified, washed with water and dried. Ethyl acetate is then removed under vaccuum to yield a crude bicarbonate soluble, biologically active oligomeric mixture.

The new technique according to the teachings of subject invention is illustrated by the following two examples which should be regarded as being carried out under a representative set of conditions rather than an exclusive set of conditions that will result in the conversion of the Ethyl Analog (E.A.) into the described oligomeric mixture. It should be further understood that changes in the concentration of either the Ethyl Analog or potassium hydroxide solution as well as the reaction temperature and times are inter-dependent so that a change in one of the above variables can be compensated by a corresponding change in the other variables. However, exosure to sufficient atmospheric oxygen is considered to be essential for maximum conversion to a sodium bicarbonate soluble oligomeric mixture under the reaction conditions described below. This can be readily accomplished if the reaction is carried out open to the atmosphere accompanied by vigorous stirring of the reaction mixture. The method is illustrated by the following examples:

EXAMPLE 1

To 500 milligrams (mg) of 3-(trans-3-keto-1-pentenyl)-2-ethyl-2-cyclopentenone (the Ethyl Analog or E.A.) in 10 milliliters (1 milliliter = 1 mL = $10^3$ liter) of absolute or pure ethanol is added 10 milliliters (mL) of 2 M (molar) potassium hydroxide solution in an unstoppered round bottom flask maintained at 50° C. in a constant temperature bath to obtain 500 milligrams of the Ethyl Analog in 20 mL of 1 M (molar) ethanolic potassium hydroxide solution Reaction was observed to start immediately and the process of the conversion to a bicarbonate soluble oligomeric mixture was monitored by ultraviolet spectroscopy which is well known in the prior art and need not be discussed here. When the conversion was judged to be sufficiently complete (ca.-3–6 hours), the reaction was quenched by the addition of dilute hydrochloric acid and the pH of the reaction mixture was adjusted to 3. The quenched reaction mixture was diluted with water and extracted several times with ethyl acetate. The combined ethyl acetate extracts were extracted with 0.1M (molar) sodium bicarbonate ($NaHCO_3$) solution. The combined sodium bicarbonate extracts were acidified with dilute hydrochloric acid to adjust the pH of the solution to 3, then extracted with ethyl acetate. The combined ethyl acetate extracts were washed with water, dried and the ethyl acetate was removed under vacuum to yield about 80–85 percent crude sodium bicarbonate soluble oligomeric mixture which is biologically active.

The crude oligomeric mixture thus obtained was chromatographed on Sephadex LH-20 using methanol as the carrier solvent. Resolution of the oligomeric mixture was not observed so that five somewhat arbitrarily selected fractions were collected. Activity in the protection of oxidative phosphorylation in isolated mitochondria was observed through all five fractions with varying degree. The highest activity was obtained in two of the five arbitrarily selected fractions. No inhibition was observed at high concentration of the oligomer.

EXAMPLE 2

Alternatively, an equivalent weight of a higher molecular weight sodium bicarbonate insoluble oligomeric mixture prepared as described and claimed in my copending patent application can be subjected to the same experimental conditions as in the above-described example to give a greater than 70 percent conversion to a sodium bicarbonate soluble oligomeric mixture.

Briefly stated, conversion of the Ethyl Analog (E.A.) under mild conditions of temperature is accomplished by mixing the Ethyl Analog with ethanolic solution of sodium hydroxide. The reaction is then quenched by using hydrochloric acid. The reaction mixture is diluted with water and extracted several times with ethyl acetate which in turn was further extracted with sodium bicarbonate solution. The combined sodium bicarbonate extracts were acidified with dilute hydrochloric acid and extracted with ethyl acetate. The ethyl acetate extracts were then washed with water, dried and after removal of ethyl acetate under vacuum yielded 80 to 85 percent crude sodium bicarbonate soluble oligomeric mixture.

Many modifications and variations of the present invention are possible in light of the above teachings. As an example, the reaction can proceed under different sets of conditions involving other concentrations of either the Ethyl Analog or potassium hydroxide solution as well as the reaction temperature and time of reaction. It is thus understood that within the scope of the appended claims the invention may be practiced otherwise than as specifically described.

What is claimed is:

1. A method for synthesizing biologically active aligomeric mixture exhibiting protection of oxidative phosphorylation of degenerated mitochondria and said oligomeric mixture being sodium bicarbonate soluble by an oligomerization reaction of prostaglandin analogs represented by the formula:

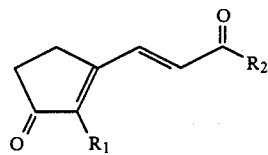

where $R_1$ and $R_2$ are members of the alkyl group.
said method includes the steps of:
treating said prostaglandin analogs with ethanolic potassium hydroxide solution with exposure to atmospheric oxygen at 50° C. under relatively mild conditions of, time and concentration to start the oligomeric reaction;
quenching the oligomeric reaction by changing the pH of the reaction mixture by means of an acid;
extracting the reaction mixture with ethyl acetate, treating ethyl acetate extract with 0.1M sodium bicarbonate; and
removing ethyl acetate under vacuum.

2. The method of claim 1 wherein the steps enumerated therein are applied to Ethyl Analog as the prostaglandin analog designated by the formula:

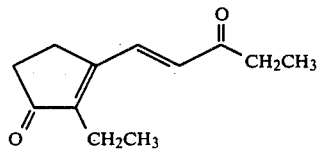

3. The method of claim 2 wherein said ethanolic potassium hydroxide solution is obtained by diluting a fixed volume of 2M potassium hydroxide solution with an equal volume of ethanol.

4. The method of claim 3 wherein the quenching of the oligomeric reaction is accomplished by treating the reaction mixture with hydrochloric acid to reduce the pH thereof to 3.

5. The method of claim 4 wherein the step of extracting with ethyl acetate further includes treating the sodium bicarbonate extracts with hydrochloric acid to make the oligomeric mixture acidic.

* * * * *